(12) United States Patent
Akao

(10) Patent No.: US 9,636,373 B1
(45) Date of Patent: May 2, 2017

(54) KAVA-BASED BEVERAGE COMPOSITION

(71) Applicant: Kahouokalani Akao, Kaneohe, HI (US)

(72) Inventor: Kahouokalani Akao, Kaneohe, HI (US)

(*) Notice: Subject to any disclaimer, the term of this patent is extended or adjusted under 35 U.S.C. 154(b) by 0 days.

(21) Appl. No.: 15/057,097

(22) Filed: Feb. 29, 2016

Related U.S. Application Data

(60) Provisional application No. 62/293,307, filed on Feb. 9, 2016.

(51) Int. Cl.
| | |
|---|---|
| *A61K 36/185* | (2006.01) |
| *A61K 36/28* | (2006.01) |
| *A61K 36/67* | (2006.01) |
| *A61K 36/77* | (2006.01) |
| *A61K 31/366* | (2006.01) |
| *A61K 31/357* | (2006.01) |
| *A61K 31/522* | (2006.01) |
| *A61K 36/258* | (2006.01) |
| *A23L 2/52* | (2006.01) |

(52) U.S. Cl.
CPC ............. *A61K 36/77* (2013.01); *A23L 2/52* (2013.01); *A61K 31/357* (2013.01); *A61K 31/366* (2013.01); *A61K 31/522* (2013.01); *A61K 36/185* (2013.01); *A61K 36/258* (2013.01); *A61K 36/28* (2013.01); *A61K 36/67* (2013.01); *A23V 2002/00* (2013.01)

(58) Field of Classification Search
CPC ...... A61K 36/185; A61K 36/67; A61K 36/28; A61K 36/258
USPC ........................................... 424/725
See application file for complete search history.

(56) References Cited

U.S. PATENT DOCUMENTS

| | | | |
|---|---|---|---|
| 5,770,207 A | 6/1998 | Bewicke | |
| 6,312,736 B1 | 11/2001 | Kelly | |
| 2006/0083795 A1* | 4/2006 | Shatkina | A23L 1/236 424/725 |
| 2006/0112584 A1* | 6/2006 | Jones | A23B 7/02 34/60 |
| 2006/0134300 A1* | 6/2006 | Newman | A23F 5/243 426/590 |
| 2008/0057161 A1* | 3/2008 | Brucker | A23F 5/14 426/73 |
| 2008/0233245 A1* | 9/2008 | White | A23L 1/296 426/73 |
| 2009/0306222 A1* | 12/2009 | Burton | A23L 1/3002 514/763 |
| 2010/0247564 A1* | 9/2010 | Lee | A61K 36/03 424/195.17 |

* cited by examiner

*Primary Examiner* — Chris R Tate
(74) *Attorney, Agent, or Firm* — Ruttler Mills, PLLC; James J. Ruttler

(57) ABSTRACT

This invention relates generally to a composition, and more specifically, to a kava-based beverage composition. In one embodiment, a beverage composition includes, but is not limited to, water; kava extract present in an approximate amount of 23.6 mg to 28.8 mg per ounce of water (e.g. yielding 7 mg to 8.6 mg of kavalactones per ounce of water or around 126 mg of kavalactones per 16 ounces of water); milk thistle extract present in an approximate amount of 4 mg to 4.8 mg per ounce of water; and yerba mate extract present in an approximate amount of 2 mg to 2.4 mg per ounce of water.

19 Claims, No Drawings

KAVA-BASED BEVERAGE COMPOSITION

PRIORITY CLAIM

This application claims the benefit of and/or priority to U.S. provisional patent application Ser. No. 62/293,307 filed Feb. 9, 2016. The foregoing application is incorporated by reference in its entirety as if fully set forth herein.

FIELD OF THE INVENTION

This invention relates generally to a composition, and more specifically, to a kava-based beverage composition.

SUMMARY

This invention relates generally to a composition, and more specifically, to a kava-based beverage composition. In one embodiment, a beverage composition includes, but is not limited to, water; kava extract (e.g., aqueous or powdered kava extract) present in an approximate amount of 23.6 mg to 28.8 mg per ounce of water (e.g. yielding 7 mg to 8.6 mg of kavalactones per ounce of water or around 126 mg of kavalactones per 16 ounces of water); milk thistle extract present in an approximate amount of 4 mg to 4.8 mg per ounce of water; and yerba mate extract present in an approximate amount of 2 mg to 2.4 mg per ounce of water.

In another embodiment, a powder herbal composition includes, but is not limited to, from about 49% to 59% by weight of kavalactones; from about 27% to 33% by weight of milk thistle extract; and from about 13% to 17% by weight of yerba mate extract.

In a further embodiment, a beverage composition includes, but is not limited to, water; a kavalactone compound; a liver detoxification compound; and a stimulant compound.

DETAILED DESCRIPTION

This invention relates generally to a composition, and more specifically, to a kava-based beverage composition. Specific details of certain embodiments of the invention are set forth in the following description to provide a thorough understanding of such embodiments. The present invention may have additional embodiments, may be practiced without one or more of the details described for any particular described embodiment, or may have any detail described for one particular embodiment practiced with any other detail described for another embodiment.

The beverage composition disclosed herein is useful for providing hydration with synergistic beneficial effects. Notably, the beverage composition includes kava which elevates mood and provides relief from stress, panic, anxiety, pain, fatigue, epilepsy, heart disease, insomnia, migranes, depression, and/or social anxiety. The beverage composition also includes caffeine which provides an elevated state of alertness, increased memory, and/or relief from exhaustion. The specific amounts of kava and caffeine present in the beverage composition work together to provide synergistic effects. The kava counteracts negative side-effects of the caffeine, such as reducing jitters and anxiousness and/or lowering blood pressure. The caffeine counteracts negative side-effects of kava, such as reducing grogginess and/or protecting against liver toxicity. Thus, the kava and the caffeine of the beverage composition synergistically work together to balance out the negative side-effects of the other while maintaining their respective benefits. In addition to the kava and caffeine, the beverage composition further includes a liver detoxification compound, such as milk thistle extract. The liver detoxification compound is present in an substantially ineffective amount per serving size of the beverage composition such that a recommended daily dosage of the liver detoxification compound is reached cumulatively when the beverage composition is over-consumed or abused. Thus, in addition to the aforementioned benefits, the beverage composition additionally provides enhanced protection against liver toxicity and/or promotes healthy liver function when the beverage composition is excessively consumed or abused. Therefore, beneficial effects of the beverage composition include relief from various ailments, elevated mood and alertness and energy—without jitters, crashes, or anxiousness and while protecting and/or promoting health of the liver.

In one embodiment, a powder herbal composition includes, but is not limited to, kava extract (e.g. kavalactones); milk thistle extract; and yerba mate extract. The powder herbal composition can be mixed with water to provide a beverage composition. Various proportions may be used for each of the extracts. For example, the kavalactones may be present in an amount from about 29% to 79% by weight, or more specifically, from about 39% to 69% by weight, or even more specifically from about 49% to 59% by weight. Significant synergistic effects have been found using about 54% of kavalactones by weight. Additionally, for example, milk thistle extract may be present in an amount from about 7% to 53% by weight, or more specifically, from about 17% to 43% by weight, or even more specifically from about 27% to 33% by weight. Significant synergistic effects have been found using about 30% of milk thistle extract by weight. Moreover, for example, yerba mate extract may be present in an amount from about 1% to 37% by weight, or more specifically, from about 3% to 27% by weight, or even more specifically from about 13% to 17% by weight. Significant synergistic effects have been found using about 15% of yerba mate extract by weight.

In another embodiment, a beverage composition includes, but is not limited to, water; kava extract containing kavalactones; milk thistle extract; and yerba mate extract. The water can be purified water, filtered water, fortified water, distilled water, or the like, or can even be another liquid such as dairy milk, coconut water, almond milk, hemp milk, rice milk, or soy milk. Additionally, the water can include beneficial bacteria (e.g., fermented kefir or kombucha). Various amounts of each of the extracts may be present.

For example, the kavalactones may be present in an amount from about 5.4 mg to 10.2 mg per ounce of water, or more specifically, from about 6.2 mg to 9.4 mg per ounce of water, or even more specifically from about 7 mg to 8.6 mg per ounce of water. For instance, the kavalactones in certain embodiments are present in an approximate amount between 60 mg and 2016 mg for the range of 8 ounces to 128 ounces of water. Significant synergistic effects have been found using about 7.8 mg of kavalactones per ounce of water.

In certain embodiments, the kavalactones are a constituent of kava extract (approximately 30% by weight of kavalactones to aqueous kava extract). Thus, in some embodiments, the kava extract is present in an amount from about 18.5 mg to 32 mg per ounce of water, or more specifically, from about 21 mg to 31.4 mg per ounce of water, or even more specifically from about 23.6 mg to 28.8 mg per ounce of water. Significant synergistic effects have been found using about 26.2 mg of kava extract per ounce of water.

Sources of kava extract include KELAI from EPI ISLAND, BOROGU from MALEKULA and PENTECOST, PHIA from TANNA, and/or KAOLIK from TANNA. The extract can include 100% stump root powder, 100% lateral roots powder, a 50/50 blend of stump and lateral roots powder, an aqueous extract, an alcohol extract, and/or kava honey. A preferred extract includes a blend of 80% stump and 20% lateral root kava extract powder containing about 30% by weight of kavalactones.

Additionally, for example, milk thistle extract may be present in an amount from about 3.2 mg to 5.6 mg per ounce of water, or more specifically, from about 3.6 mg to 5.2 mg per ounce of water, or even more specifically from about 4 mg to 4.8 mg per ounce of water. For instance, the milk thistle extract in certain embodiments is present in an approximate amount between 35 mg and 2240 mg for the range of 8 ounces to 128 ounces of water. Significant synergistic effects have been found using about 4.4 mg of milk thistle extract per ounce of water.

Moreover, for example, yerba mate extract may be present in an amount from about 1.6 mg to 2.8 mg per ounce of water, or more specifically, from about 1.8 mg to 2.6 mg per ounce of water, or even more specifically from about 2 mg to 2.4 mg per ounce of water. For instance, the yerba mate extract in certain embodiments is present in an approximate amount between 17 mg and 300 mg for the range of 8 ounces to 128 ounces of water. Significant synergistic effects have been found using about 2.2 mg of yerba mate extract per ounce of water.

In a further embodiment, a beverage composition includes, but is not limited to, water; a kavalactone compound; a liver detoxification compound; and a stimulant compound.

In some embodiments, the kavalactone compound can include any of the following types: Yangonin, 10-methoxyyangonin, 11-methoxyyangonin, 11-hydroxyyangonin, Desmethoxyyangonin, 11-methoxy-12-hydroxydehydrokavain, 7,8-dihydroyangonin, Kavain, 5-hydroxykavain, 5,6-dihydroyangonin, 7,8-dihydrokavain, 5,6,7,8-tetrahydroyangonin, 5,6-dehydromethysticin, Methysticin, and/or 7,8-dihydromethysticin. In some embodiments, the kavalactone is a constituent compound of kava extract. Kava extract can include extract from the kava root, stump, or basal stem. For instance, kava extract can include root extract from a root containing approximately 15%-45% by weight of kavalactones or more specifically about 30% by weight of kavalactones.

In one embodiment, a liver detoxification compound can include a silymarin complex or any of the following constituents: silybin A, silybin B, isosilybin A, isosilybin B, silychristin, isosilychristin, silydianin, and/or taxifolin. In another embodiment, a liver detoxification compound can include a silibinin complex or any of the following constituents: silybin A and/or silybin B. In one embodiment, a liver detoxification compound is a constituent compound of milk thistle seed extract. For instance milk thistle extract can include extract from a seed containing approximately 4-6% by weight of silymarin. In other embodiments, a liver detoxification compound can include any of the following extracts: milk thistle, borututu bark, burdock root, and/or dandelion root.

In one embodiment, a stimulant compound can include caffeine. In one embodiment, a stimulant compound is a constituent compound of extract from yerba mate leaves. For instance yerba mate extract can include extract from a leaf containing approximately 0.7-1.7% by weight of caffeine. In another embodiment, a liver detoxification compound is a constituent compound of extract from guarana leaves. For instance guarana extract can include extract from a leaf containing approximately 2.5-7.6% by weight of caffeine.

In embodiments including kava extract, milk thistle extract, and/or yerba mate extract, other constituent compounds naturally present within the respective extract may also be included in the beverage compound. Alternatively, any of the naturally present compounds can be selectively removed.

In another particular embodiment of the beverage composition also includes, but is not limited to, *ginseng* extract, a vitamin, a mineral, a flavoring agent, a coloring agent, and/or a sweetener. For example, any of the following may be present in the beverage composition: vitamin C, vitamin D, niacin, vitamin B3, vitamin B5, vitamin B6, vitamin B12, pantothenic acid, magnesium, zinc, sodium, *ginseng* (e.g., from *ginseng* root extract), sugar, white grape juice, malic acid, *stevia* (e.g., from *stevia* leaf extract), fruit punch flavor, lemonade, pink lemonade, coloring, fruit juice, vegetable juice, and/or kava honey.

Kavalactones are known to have beneficial properties useful for treating various ailments, each based on certain recommended daily dosage amounts. For instance, the following Table 1 illustrates certain representative ailments and approximate daily dosage amounts of kavalactones for treating each respective ailment. The recommended dosage amounts are approximates and can be higher or lower depending on individual characteristics.

TABLE 1

| Ailment | Kavalactone Dosage |
| --- | --- |
| Anxiety and Panic | 250-500 mg 2-3 times per day |
| Pain | 250-350 mg 3 times per day |
| Chronic Fatigue Syndrome | 250 mg 3 times per day |
| Depression | 250 mg 2-3 times per day |
| Epilepsy | 250 mg 2 times per day |
| Heart Disease | 250 mg 3 times per day |
| Insomnia | 250-500 mg at bedtime |
| Migraine | 250 mg 3 times per day |
| Stress | 250-500 mg 1-3 times per day |

In certain embodiments, approximately 126 mg of kavalactones are provided within a 16 ounce beverage composition. Such level of kavalactones permits effective treatment of many of these and other ailments based on an average consumption rate of approximately 1-6 units of the 16 ounce beverage compositions. Of course, smaller size beverage compositions may be provided with more kavalactones or larger size beverage compositions may be provided with fewer kavalactones. The 16 ounce beverage composition size is representative in that it is typical of many other consumer beverage sizes. It is not intended to be limiting. In this example, 6 of the 16 ounce beverage compositions would yield around 750 mg of kavalactones, which is within a safe consumption range for kavalactones per day (e.g., around 300-800 mg of kavalactones are considered safe for consumption).

However, excessive consumption of kavalactones may cause or contribute to liver damage or toxicity, such as approximately 800 mg of kavalactones or more per day. In certain embodiments, this amount of kavalactones would be exceeded after approximately six of the 16 ounce beverage compositions each containing approximately 126 mg of kavalactones. For instance, consumption of a 24 pack or 1 case of 16 ounce beverage compositions would result in consumption of approximately 3024 mg of kavalactones, which would be in excess of the recommended daily consumption amount of kavalactones. Moreover, the recommended daily consumption amount of kavalactones is close to exceeded with just six of the 16 ounce beverage compositions at approximately 750 mg of kavalactones.

Therefore, in certain embodiments, milk thistle extract, which can protect against and/or treat liver toxicity or damage, is provided in the beverage compositions in a relatively ineffective amount such that the recommended dosage of milk thistle extract is cumulatively reached at around the time of daily overconsumption of kavalactones (e.g., after around six of the 16 ounce beverage compositions in this example). For instance, approximately 70 mg of milk thistle extract is provided per 16 ounces of beverage composition. This 70 mg of milk thistle extract is below the recommended daily dosage amount of approximately 160-800 mg for protection against and/or treatment of liver toxicity or damage. Therefore, a single 16 ounce beverage composition containing approximately 70 mg of milk thistle extract is on its own substantially ineffective for protecting against and/or treating for liver toxicity or damage. However, consuming additional 16 ounce units of the beverage composition yields additional cumulative amounts of milk thistle extract. Continuing the example, after approximately six of the 16 ounce beverage compositions there would be cumulative consumption of approximately 420 mg of milk thistle extract. And, after approximately 24 of the 16 ounce beverage compositions (1 case) there would be cumulative consumption of approximately 560 mg of milk thistle extract. These daily amounts of milk thistle extract are within recommended daily dosage amounts of approximately 160-800 mg of milk thistle extract (e.g, 360 mg of milk thistle extract was deemed effective). These cumulative daily amounts of milk thistle extract are reached concomitantly with high to excessive levels of kavalactones from multiple beverage unit consumptions that could cause or contribute to liver toxicity and/or damage. Thus, the formulation of relative amounts of kavalactones and milk thistle extract enables high consumption levels of the beverage while protecting against and/or treating liver toxicity or damage that could otherwise occur.

While kavalactones have beneficial properties as discussed herein, they also can have side effects as discussed herein, such as drowsiness or lethargy. Accordingly, in addition to the kavalactones and milk thistle extract, yerba mate extract is provided to counter certain potential side effect. For instance, approximately 35 mg of yerba mate extract is present per 16 ounces of beverage composition. This amount of yerba mate extract helps balance negative side effects of kavalactone consumption, but also results in less than the recommended dosage amount of yerba mate extract (e.g., around 1000-1500 mg per day) when the beverage composition is excessively used or overconsumed. For instance, cumulative consumption of yerba mate extract is approximately 210 mg for six of the 16 ounce beverage compositions and approximately 840 mg for 24 (1 case) of the 16 ounce beverage compositions. The yerba mate extract itself may introduce certain side effects as discussed herein, but at the provided relative amounts the kavalactones synergistically counter these side effects of the yerba mate extract. Together, the specified amounts of each of the kavalactones, milk thistle extract, and yerba mate work together to provide benefits while minimizing or eliminating negative side effects of one another. The following examples illustrate the example relative amounts of kavalactones, milk thistle extract, and yerba mate extract discussed herein.

EXAMPLE 1

A beverage composition contains the following amounts of water, kava extract/kavalactones, yerba mate extract, and milk thistle extract (Table 2). Modifications to the amounts of each ingredient are possible as discussed herein. Furthermore, additional ingredients may be added, substituted, and/or any of the specified ingredients may be removed as also discussed herein.

TABLE 2

| Ingredient | Amount |
| --- | --- |
| water | 16 ounces total volume including volume of other ingredients |
| kava extract | 420 mg (yielding approximately 126 mg of kavalactones) |
| yerba mate extract | 35 mg |
| milk thistle extract | 70 mg |

The following Table 3 indicates cumulative amounts of each of the kavalactones, yerba mate extract, and milk thistle extract following consumption of multiple 16 ounce units of the beverage composition. Table 3 also provides recommended daily amounts of each of the kavalactones, yerba mate extract, and milk thistle extract. As shown, the beverage composition provides the benefits of kavalactones while balancing, preventing, treating, and/or guarding against some of the negative side effects possible after consumption of around 2-6 beverage composition units daily.

TABLE 3

| Daily Consumption | Kavalactones | Milk Thistle Extract | Yerba Mate Extract |
| --- | --- | --- | --- |
| 1 16 ounce bottle | 126 mg | 70 mg | 35 mg |
| 2 16 ounce bottle | 252 mg | 140 mg | 70 mg |
| 6 16 ounce bottles | 750 mg | 420 mg | 210 mg |
| 24 16 ounce bottles | 3024 mg | 1680 mg | 840 mg |
| Recommended Daily Amount | 300-800 mg | 160-800 mg | 1000-1500 mg |

EXAMPLE 2

A beverage composition containing the amounts of water, supplement blend (e.g., kava extract/kavalactones, yerba mate extract, milk thistle extract, and other vitamins, minerals, and/or herbal extracts), and other flavoring/coloring ingredients as provided in Table 4. Modifications to the amounts of each ingredient are possible as discussed herein. Furthermore, additional ingredients may be added, substituted, and/or any of the specified ingredients may be removed as discussed herein. The composition is prepared by a process of blending all the ingredients by dissolving each ingredient completely before adding another. The resultant composition is hot filled into final packaging.

TABLE 4

| Ingredient | Percent by Weight | Weight Per 1000 Gallons | Gallons |
| --- | --- | --- | --- |
| Filtered Water | 93.0 | 7931.8 | 953.1 |
| Supplement Blend | 0.2 | 23.3 | |

TABLE 4-continued

| Ingredient | Percent by Weight | Weight Per 1000 Gallons | Gallons |
|---|---|---|---|
| Granulated Sugar | 3.0 | 255 | |
| White Grape Juice Concentrate | 3.0 | 255 | |
| Malic Acid | 0.1 | 8.5 | |
| Stevia Leaf Extract | 0.01 | 0.9 | |
| Fruit Punch Flavor | 0.2 | 17 | |
| Lemonade Pink Flavor | 0.05 | 4.3 | |
| EXBERRY shade "red" | 0.04 | 3.4 | |

Many of the ingredients listed in Table 4 can be obtained from suppliers such as ALLEN FLAVORS, ENCORE FRUIT (DELANO GROWERS), and GNT. The beverage composition includes the following supplement blend expanded in Table 5 (measurements provided per 8 fluid ounces).

TABLE 5

Supplement Facts
Serving Size 8 fl oz (240 mL)
Serving Per Container 2

| | Amount Per Serving | % Daily Value |
|---|---|---|
| Calories | 50 | |
| Total Carbohydrate | 12 g | 4% |
| Sugars | 12 g | ** |
| Vitamin C (ascorbic acid) | 30 mg | 50% |
| Vitamin D (cholecalciferol) | 40 IU | 10% |
| Niacin (niacinamide) | 10 mg | 50% |
| Vitamin B6 (pyridoxine hydrochloride) | 1 mg | 50% |
| Vitamin B12 (cyanocobalamin) | 3 mcg | 50% |
| Pantothenic Acid (d-calcium pantothenate) | 5 mcg | 1% |
| Magnesium (magnesium lactate) | 5 mg | 1% |
| Zinc (zinc aspartate) | 1 mg | 4% |
| Proprietary Blend Kava Root Extract, Milk Thistle Extract, Ginseng Extract, Caffeine (from Yerba Mate) | 295 mg | ** |

*Percent Daily Values are based on a 2,000 calorie diet.
** Daily Value not established.
Contains: 17 mg of Caffeine The beverage composition has the following properties provided in Table 6.

TABLE 6

| Parameter | Value |
|---|---|
| Product Density | 8.5 lbs/gallon |
| pH | 3.2 +/− 0.20 |
| Brix | 5.40 +/− 0.20 |
| Taste | Herbal Fruit Punch |
| Appearance | Pink Liquid |

While preferred and alternate embodiments of the invention have been illustrated and described, as noted above, many changes can be made without departing from the spirit and scope of the invention. For instance, the beverage composition can be in a form of a powder, pill, tablet, capsule, frozen concentrate, or liquid concentrate without any water or with only minimal amounts of water. The beverage composition can be packaged in a can, bottle, or other consumer packaging. Alternatively, the beverage composition can be provided in a powdered read-to-mix package. Additionally, the beverage composition can be integrated within a food stuff such as yogurt, gum, a snack bar, or other food product. In certain embodiments, the beverage composition can include a preservative, buffering agent, stabilizing agent, fiber, fruit or vegetable chunks, or other additive. In some embodiments, any of the following sweetening agents may be included: sugar, honey, fruit, syrup, acesulfame, xylitol, alitame, aspartame, cyclamate, glycyrrhizin, luo han guo, neotame, perillartine, saccharin, stevioside, sucralose, and/or extract of maple, beet, sorghum, corn, cane, coconut, barley, molasses, brown rice, agave, *stevia*, yacon, or other similar sweetening agent. In some embodiments, the beverage composition can include any of the following types of preservatives: sodium benzoate, potassium sorbate, benzoate, nitrite, sulphite, sorbate, and/or other similar preservative. In certain embodiments, the beverage composition can include one or more of the following types of flavoring agents: peach, pineapple, apple, banana, blackberry, blackcurrant, blueberry, boysenberry, cantaloupe, cherry, cranberry, date, fig, gooseberry, grapefruit, grape, guava, kiwi, lemon, lime, loganberry, mango, mulberry, nectarine, orange, *papaya*, passionfruit, peach, pear, pineapple, plum, pomegranate, raspberry, starfruit, strawberry, watermelon, tomato, carrot, and/or other similar natural or artificial flavoring agent. In other embodiments, the beverage composition includes any of the following types of buffering agents: phosphoric acid, sodium citrate, potassium citrate, potassium tartrate, and/or other similar buffering agent. In further embodiment, the beverage composition includes one or more of the following types of nutritional additives: vitamins, minerals, antioxidants, nutrients, fiber, or other similar additive. In some embodiments, the beverage composition includes one or more of a stabilizing agent, a coloring agent, and/or carbonation. In certain embodiments, the beverage composition can include any adaptogen and any part of the adaptogen (e.g., extract of leaf, stem, seed, bark, stump, flower, and/or root).

Note that various examples and embodiments disclosed herein discuss volumes of water. In such examples and embodiments, the total volume of water may be less that that specified due to the volume of the ingredients (e.g., the total volume of the ingredients and the water may be 16 ounces, but the actual water content may be slightly less than 16 ounces due to the volume of the ingredients themselves).

Accordingly, the scope of the invention is not limited by the disclosure of these preferred and alternate embodiments. Instead, the invention should be determined entirely by reference to the claims that follow.

What is claimed is:

1. A beverage composition comprising:
   water;
   kava extract present in an approximate amount of 26.5 mg per ounce of the water;
   milk thistle extract present in an approximate amount of 4.4 mg per ounce of the water; and
   yerba mate extract present in an approximate amount of 2.2 mg per ounce of the water.

2. The beverage composition of claim 1, further comprising:
   vitamin C.

3. The beverage composition of claim 1, further comprising:
   vitamin D.

4. The beverage composition of claim 1, further comprising:
   niacin.

5. The beverage composition of claim 1, further comprising:
vitamins B6 and B12.

6. The beverage composition of claim 1, further comprising:
pantothenic acid.

7. The beverage composition of claim 1, further comprising:
magnesium.

8. The beverage composition of claim 1, further comprising:
zinc.

9. The beverage composition of claim 1, further comprising:
sugar.

10. The beverage composition of claim 1, further comprising:
white grape juice concentrate.

11. The beverage composition of claim 1, further comprising:
malic acid.

12. The beverage composition of claim 1, further comprising:
*stevia* leaf extract.

13. The beverage composition of claim 1, further comprising:
fruit punch flavoring agent.

14. The beverage composition of claim 1, further comprising:
pink lemonade flavoring agent.

15. The beverage composition of claim 1, further comprising:
red coloring agent.

16. The beverage composition of claim 1, wherein the beverage composition has a density of approximately 8.5 lbs/gallon.

17. The beverage composition of claim 1, wherein the beverage composition has a pH of approximately 3.2.

18. The beverage composition of claim 1, wherein the beverage composition has a brix of approximately 5.4.

19. A beverage composition comprising:
water present in an approximate amount of 16 ounces;
kava extract present in an approximate amount of 420 mg per the approximately 16 ounces of water;
milk thistle extract present in an approximate amount of 70 mg per the approximately 16 ounces of water; and
yerba mate extract present in an approximate amount of 35 mg per the approximately 16 ounces of water.

* * * * *